(12) United States Patent
Bjornsson et al.

(10) Patent No.: US 8,835,156 B2
(45) Date of Patent: Sep. 16, 2014

(54) PRETREATMENT OF NON-WOOD LIGNOCELLUIOSIC MATERIAL

(75) Inventors: Lovisa Bjornsson, Lund (SE); Sven-Erik Svensson, Lund (SE); Sanam Monavari, Lund (SE); Emma Kreuger, Lund (SE); Guido Zacchi, Malmo (SE)

(73) Assignee: Sekab E-Technology AB (SE)

( * ) Notice: Subject to any disclaimer, the term of this patent is extended or adjusted under 35 U.S.C. 154(b) by 255 days.

(21) Appl. No.: 13/381,380

(22) PCT Filed: Jun. 17, 2010

(86) PCT No.: PCT/EP2010/058563
§ 371 (c)(1),
(2), (4) Date: Mar. 7, 2012

(87) PCT Pub. No.: WO2011/000712
PCT Pub. Date: Jan. 6, 2011

(65) Prior Publication Data
US 2012/0156727 A1    Jun. 21, 2012

(30) Foreign Application Priority Data
Jul. 3, 2009 (EP) .................................... 09164571

(51) Int. Cl.
| | | |
|---|---|---|
| *C02F 3/34* | (2006.01) | |
| *C12N 1/22* | (2006.01) | |
| *C12N 1/38* | (2006.01) | |
| *C12P 1/00* | (2006.01) | |
| *C12P 7/00* | (2006.01) | |
| *C12P 7/06* | (2006.01) | |
| *D21C 1/00* | (2006.01) | |
| *C12P 5/02* | (2006.01) | |
| *C12P 7/10* | (2006.01) | |
| *C12P 7/14* | (2006.01) | |
| *D21C 1/04* | (2006.01) | |
| *D21C 5/00* | (2006.01) | |

(52) U.S. Cl.
CPC .. *C12P 7/14* (2013.01); *Y02E 50/16* (2013.01); *D21C 5/005* (2013.01); *C12P 5/023* (2013.01); *Y02E 50/343* (2013.01); *C12P 2201/00* (2013.01); *C12P 7/10* (2013.01); *D21C 1/04* (2013.01); *Y02E 50/17* (2013.01); *D21C 5/00* (2013.01)
USPC ........... 435/277; 435/132; 435/161; 435/244; 435/252; 435/262; 435/267

(58) Field of Classification Search
None
See application file for complete search history.

(56) References Cited

PUBLICATIONS

Chen Y. et al., "Ensiling Agricultural Residues for Bioethanol Production", *Applied Biochemistry and Biotechnology*, vol. 143, 2007, pp. 80-92.
International Preliminary Report on Patentability Corresponding to International Application No. PCT/EP2010/058563; Date of Issuance: Jan. 4, 2012; 7 Pages.
International Search Report Corresponding to International Application No. PCT/EP2010/058563; Date of Mailing; Dec. 13, 2010; 3 Pages.
Joelsson E. et al., "Combined production of bioethanol and biogas from wheat straw using weak organic acid hydrolysis pretreatment", *The 32nd Symposium on Biotechnology for Fuels and Chemicals*, Apr. 19-22, 2010, Retrieved from the internet on Nov. 1, 2012: http://sim.confex.com/sim/32nd/techprogram/P13896.HTM.
Kootstra A.M. et al., "Optimization of the dilute maleic acid pretreatment of wheat straw", *Biotechnology for Biofuels*, vol. 2, Dec. 21, 2009, pp. 1-14.
Kootstra et al., "Comparison of dilute mineral and organic acid pretreatment for enzymatic hydrolysis of wheat straw", *Biochemical Engineering Journal*, vol. 46, Oct. 2009, pp. 126-131.
Linde M. et al., "Steam pretreatment of dilute $H_2SO_4$-impregnated wheat straw and SSF with low yeast and enzyme loadings for bioethanol production", *Biomass and Bioenergy*, vol. 32, 2008, pp. 326-332.
Ren H. et al., "The Impact of Enzyme Characteristics on Corn Stover Fiber Degradation and Acid Production During Ensiled Storage", *Applied Biochemistry and Biotechnology*, vol. 136-140, 2007, pp. 221-228.
Schneider R.M. et al., "The Effects of Bacterial Inoculants, Beet Pulp, and Propionic Acid on Ensiled Wet Brewers Grains", *Journal of Dairy Science*, vol. 78, 1995, pp. 1096-1105.
Sindhu R. et al., "Formic Acid as a Potential Pretreatment Agent for the Conversion of Sugarcane Bagasse to Bioethanol", *Applied Biochemistry and Biotechnology*, vol. 162, 2010, pp. 2313-2323.
Thomsen M.H. et al., "Pretreatment of Whole-Crop Harvested, Ensiled Maize for Ethanol Production", *Applied Biochemistry and Biotechnology*, vol. 148, 2008, pp. 23-33.
Zhao R. et al., "Methane production from rice straw pretreated by a mixture of acetic-propionic acid", *Bioresource Technology*, vol. 101, Oct. 4, 2009, pp. 990-994.

*Primary Examiner* — Debbie K Ware
(74) *Attorney, Agent, or Firm* — Myers Bigel Sibley & Sajovec, P.A.

(57) ABSTRACT

The present disclosure provides a method for pre-treating non-wood lignocellulosic material containing less than 5 % (w/w) starch or sugar in a process for production of ethanol from lignocellulose, comprising the steps of: adding organic acid or organic acid-producing bacteria to the lignocellulosic material; storing the lignocellulosic material in the presence of the organic acid for a period of at least two weeks in an atmosphere of less than 5% oxygen to obtain organic acid-impregnated material; and heating the organic acid-impregnated material at a temperature of at least 160° C. to obtain pre-treated lignocellulosic material, wherein no, or substantially no, inorganic acid or base, including $SO_2$, is added in the method.

20 Claims, 1 Drawing Sheet

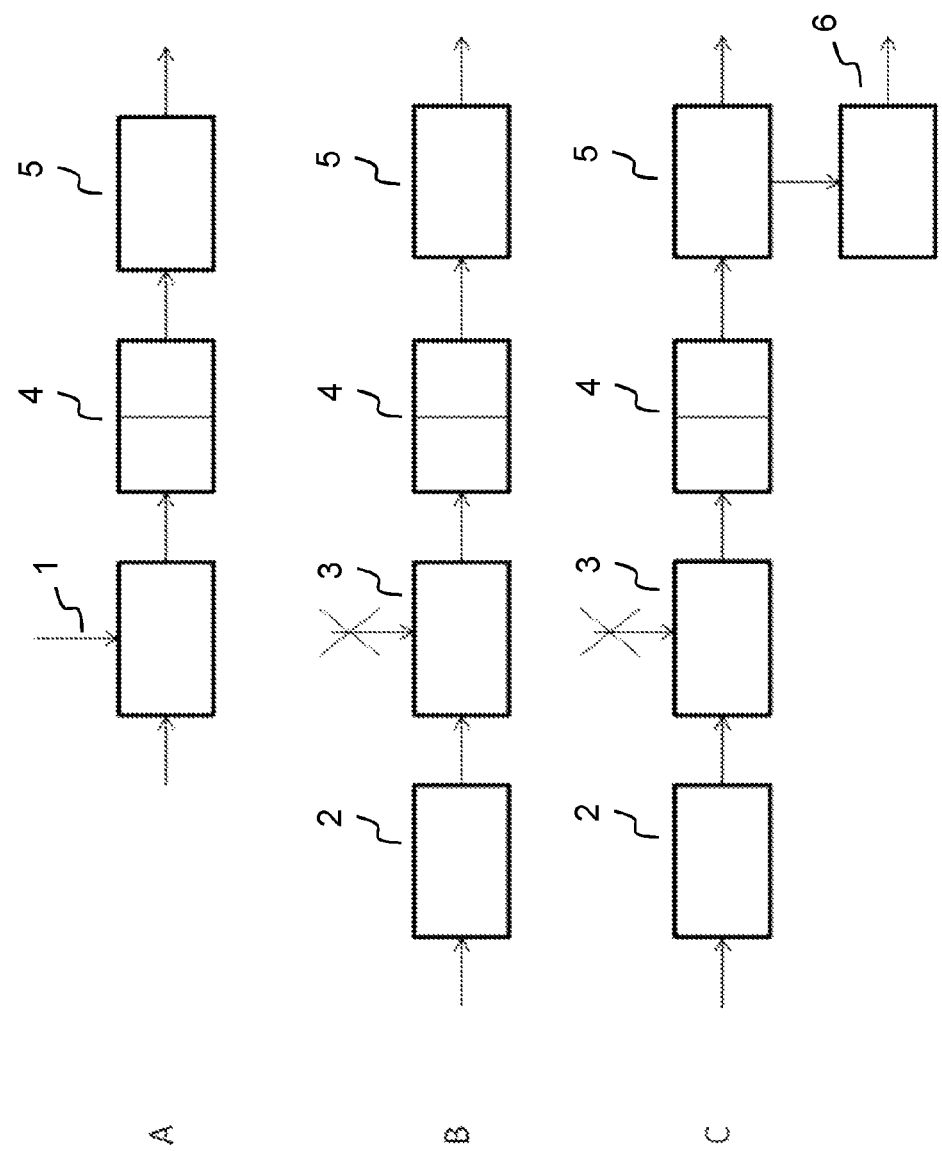

PRETREATMENT OF NON-WOOD LIGNOCELLUIOSIC MATERIAL

RELATED APPLICATIONS

This application is a 35 U.S.C. §371 national phase application of PCT Application PCT/EP2010/058563, filed Jun. 17, 2010, which claims priority to EP 09164571.3, filed Jul. 3, 2009. The entire content of each of these applications is incorporated herein by reference.

TECHNICAL FIELD

The present disclosure relates to a method for pretreatment of lignocellulosic material containing low amounts of starch and sugar in a process for ethanol production.

BACKGROUND

Global warming, petroleum depletion and energy security have been the main driving forces for the development of renewable fuels that can replace the petroleum-derived fuels, such as gasoline and diesel. Ethanol is currently the most commonly used renewable automobile fuel. It is largely produced by fermentation of sugar or starch-containing feedstocks, such as cane sugar, corn and wheat. However, the supply of these crops is relatively limited, and many of them can be considered as a human food resource. Another disadvantage is that the production of ethanol from most of these raw materials gives a relatively low net energy gain and a low renewable $CO_2$-efficiency, i.e. the amount of fossil $CO_2$ produced throughout the production chain when producing ethanol from these materials is high. Lignocellulose is a more abundant and less expensive raw material with the potential to give a higher net energy gain.

Lignocellulose is primarily composed of cellulose, hemicellulose and lignin. Cellulose is composed of polysaccharide chains of several hundred to over ten thousand linked glucose units, whereas hemicellulose is a branched polysaccharide composed of xylose, other pentose sugars and various hexose sugars. Cellulose and hemicellulose are tightly associated to lignin, a polyphenolic compound that ties the cellulose and hemicellulose polymers together, thus providing the lignocellulosic material with rigidity and mechanical strength.

In the production of ethanol from lignocellulosic materials, various pretreatment and hydrolysis steps are used to degrade the cellulose and hemicellulose polysaccharides in the lignocellulose to monosaccharides. Microorganisms can then be used to ferment the monosaccharides to ethanol. Pretreatment of lignocellulosic feedstocks can be carried out physically (mechanical comminution, pyrolysis), chemically (dilute acid, alkaline pretreatment), physicochemically (steam explosion), and biologically (fungal delignification). These methods open up the lignocellulosic multicomponent matrix and render the carbohydrate components more accessible to hydrolytic enzymes. Besides effective cellulose liberation, an ideal pretreatment has to minimize the formation of degradation products because of their inhibitory effects on subsequent hydrolysis and fermentation processes. However, several approaches for reducing the negative impact of inhibitors have been suggested.

The need for high energy, chemicals and corrosion-resistant, high-pressure reactors make pretreatment to one of the most expensive steps in cellulosic ethanol production.

A common pretreatment step is to use an inorganic acid. The spent liquid from such pretreatment needs to be purified. For example, when using $SO_2$ gas, which is considered an inorganic acid in the context of the present disclosure, during the pretreatment, the resulting spent liquid comprises sulphur which needs to be removed and taken care of. Furthermore, using an inorganic acid in the pretreatment step may entail costs and be harmful to the environment.

To summarize, there is a need in the art for improving the pretreatment in the process for production of ethanol.

Brief Description

It is an object of the present disclosure to provide for pretreatment of non-wood lignocellulosic material containing less than 5% (w/w) starch or sugar in a process for production of ethanol from lignocellulose.

Further, it is an object of some aspects of the present disclosure to provide for cost-efficient and/or environmentally friendly pretreatment of such lignocellulosic material.

In brief, there is provided a method for pre-treating non-wood lignocellulosic material containing less than 5% (w/w) starch or sugar in a process for production of ethanol from lignocellulose, comprising the steps of:
  a) adding organic acid or organic acid-producing bacteria to the lignocellulosic material;
  b) storing the lignocellulosic material in the presence of the organic acid for a period of at least two weeks in an atmosphere of less than 5% oxygen to obtain organic acid-impregnated material; and
  c) heating the organic acid-impregnated material at a temperature of at least 160° C. to obtain pre-treated lignocellulosic material, wherein no, or substantially no, inorganic acid or base, including $SO_2$, is added in the method.

Various features and embodiments of the method are described below.

Detailed Description

The method of the present disclosure relates to pretreatment of non-wood lignocellulosic material containing less than 5% (w/w) starch or sugar. Preferably, the non-wood lignocellulosic material contains less than 3% (w/w), such as less than 2% (w/w) or 1% (w/w) starch or sugar. Consequently, starch-rich or sugar-rich materials are not suitable raw materials. The reason for this is that starch and sugars are degraded during the pre-treatment method of the present disclosure, which results in a significantly reduced ethanol yield when taking the whole carbohydrate content of the raw material into account.

Starch-rich materials refer particularly to some plant-based materials, including for example wheat, barley, potato, sweet potato and corn. Suitable starting material for the method of the present disclosure may however be derived from such starch-rich materials. For example, whole crop wheat, including both the seeds (starch) and the straw (lignocellulose), is not suitable for the method of the present disclosure, while the straw taken alone is an appropriate raw material. Further, in some embodiments, lignocellulosic materials containing residual amounts (e.g. <1% (w/w)) of sugar or starch may be suitable starting materials. This is further discussed below.

In the context of the present disclosure, "lignocellulosic material" refers to plant biomass that comprises cellulose, hemicellulose, and lignin. Lignin fills the spaces in the cell wall between cellulose, hemicellulose, and pectin components. The carbohydrate polymers (cellulose and hemicelluloses) are tightly bound to the lignin, by hydrogen and covalent bonds.

The "non-wood" lignocellulosic material is not as solid as wood and lacks wood structure. In contrast to non-wood lignocellulosic material, wood is derived from the stems, branches and roots of trees. Another property of a non-wood lignocellulosic material is that its lignin content usually is lower than that of wood. The non-wood lignocellulosic material of the present disclosure may thus have a lignin content of 23% (w/w) or less. Normally, the biomass of non-wood lignocellulosic material is less than one year old. In contrast, the biomass of wood is normally more than one year old. For example, even though sugar cane plants may live for more than one year, the sugar canes are harvested more than once a year, and the biomass of the sugar canes is therefore less than one year old when harvested. In contrast, wood from trees is hardly ever harvested after less than a year; not even the fastest growing species are normally harvested earlier than after less than three to five years. The non-wood lignocellulosic material of the present disclosure may thus be derived from biomass being less than two years old, such as less than one year old, when harvested.

Examples of non-wood lignocellulosic material containing less than 5% (w/w) starch or sugar are bagass (from sugar cane or sorghum), sugar cane trash, wheat straw, rice straw, various sorghum species, arundo, mischanthus and other agricultural residues.

Sugar canes may be separated into three parts; juice (containing sugar), bagass and trash. The bagass is the fibrous residue remaining after the extraction of the sugar from the sugar cane stalks. The sugar cane trash is the remainings after the stalks have been separated from the sugar cane plants. The trash is mainly constituted by leaves.

There are numerous *Sorghum* species, about 30 different examples. Some specific examples are *Sorghum exstans, Sorghum grande, Sorghum halepense* and *Sorghum interjectum*.

In the context of the present disclosure, "organic acid" refers to an acid containing at least one carboxyl group (—COOH). Examples of organic acids are acetic acid, formic acid or lactic acid. "Organic acid-producing bacteria" refers, in the context of the present disclosure, to bacteria which produce acetic acid, formic acid or lactic acid. When the lignocellulosic material contains sugar, the organic acid-producing bacteria can produce organic acids. "Inorganic acid" refers to an acid that do not contain a carbon atom. Within the art, inorganic acids are sometimes referred to as mineral acids.

The storing of the lignocellulosic material may for example be in a container, such as a vessel or a silo, in one or more bales wrapped in plastics or another air impermeable material or in a traditional stack. A "container" refers to any construction capable of holding the material in question, and it may be comprised of different materials, such as metals (e.g. stainless steel) or concrete etc.

In the case of a container (in particular a silo) or a stack, new material may be added on top of the container or stack and organic acid-impregnated lignocellulosic material may be taken from the bottom of the container or stack. In such an arrangement, organic acid or organic acid-producing bacteria may be continuously added.

The organic acid which is present during the storing is either added in step a) or produced by the organic acid-producing bacteria added in step a) to the lignocellulosic material. In some embodiments, the organic acid may also be produced by organic acid-producing bacteria naturally occurring in the lignocellulosic material, provided that such bacteria are sufficiently abundant. The naturally occurring bacteria may for example be lactic acid bacteria.

The result from the storing is "organic acid-impregnated lignocellulosic material". The organic acid or the organic acid producing bacteria may be added once in the initial phase of the storing or successively throughout the whole or part of the storing period.

In embodiments of the present disclosure, step b) can be considered a type of ensiling.

The organic acid-impregnated lignocellulosic material is heated at a temperature of at least 160° C., preferably at least 180° C. or at least 190° C., to obtain pretreated lignocellulosic material. The heating may for example be performed for a period of at least 5 minutes, such as at least 20 minutes (the skilled person realizes relatively long periods may be beneficial when relatively low temperatures are used). However, the organic acid-impregnated lignocellulosic material may also be heated for a shorter period, such as 30 seconds to 4 minutes at a temperature of at least 210° C., such as at least 215° C. or 220° C. Consequently, the "pretreated lignocellulosic material" of the present disclosure is a lignocellulosic material which is first stored in the presence of organic acid and then heat treated.

The heating is preferably performed by adding steam into the lignocellulosic material. The heating may be performed in a pressurized vessel.

Further, during the heating, an overpressure is normally obtained, and during the heating step, the pressure may be successively increased or decreased, in some embodiments stepwise.

In some embodiments of step c), additional organic acid may be added to the lignocellulosic material. This addition is a complement to the addition of organic acid or organic acid-producing bacteria added in step a). However, in other embodiments, substantially no additional organic acid is added during step c), see below.

No, or substantially no, inorganic acid or base, including $SO_2$, is added in the method. That means that a small amount of inorganic acid or base may be added in the method, provided that the addition has no substantial impact on the reaction conditions. In the context of the present disclosure, "substantially no addition" of inorganic acid or base thus refers to addition of an amount corresponding to a pH increase or decrease in the material to which it is added of less than 0.5, preferable less than 0.3 or 0.1, which pH is measured in a liquid fraction from the material, such as liquid squeezed out of the pretreated lignocellulosic material after the completion of step c). In preferred embodiments, no inorganic acid or base at all is added in the method of the present disclosure.

Ensiling is a forage crop preservation method and is a choice for stable storage of feedstocks. During ensiling, the low pH caused by fermentation of free sugars inhibits microbes that decompose polysaccharides and thereby reduces the degradation of carbohydrates in the feedstock. The silage may contain one or more strains of lactic acid bacteria. When closely packed, the supply of oxygen is limited and attendant microorganims will exhaust the available oxygen. When the access to oxygen is low available sugars will be fermented to acids (and sometimes alcohol) by attendant fermenting mircoorganims.

Chen et al (*Appl Biochem Biotechnol.*, 2007, 143, p. 80-92) discloses a process for pretreatment of agriculture products, such as wheat straw, in the process of ethanol production. Ensiling is used as an alternative for a traditional pretreatment step, thus omitting the heating step that normally precedes the hydrolysis in production of ethanol from lignocellulose. However, the conclusion in Chen et al is that ensiling is not as effective as widely accepted chemical pretreatments.

The method according to the present disclosure is based on the inventor's insight that a traditional chemical pretreatment both entails costs and results in non-wanted waste, such as sulphur-containing waste. In the examples presented below it is shown that the results of the method of the present disclosure are equally good as, or even better than, a traditional pretreatment using $SO_2$. Without being bound by any specific scientific theory, the inventors believe that the storing in the presence of the organic acid is necessary for obtaining a satisfactory result when the pH during the heating is not as low as when $SO_2$ is used. By performing storing as a part of the pretreatment, organic acid may thus be used instead of inorganic acid.

The concept of storing the lignocellulosic material in the presence of organic acids before the heating step instead of adding an inorganic acid, such as sulfur dioxide or sulphuric acid, in connection with the heating step has several advantages, of which some are discussed below.

Acids added in the pretreatment are to a large extent retrieved in the spent liquid resulting from the distillation of the ethanol production process. One advantage of using organic acids instead of inorganic acids in the pretreatment is that the organic acids are biodegradable. Consequently, in a digestive treatment of the spent liquid, biogas, such as methane, may be produced from the organic acids. If biogas is not produced from the spent liquor, the biodegradability of the organic acids is still beneficial because it means that they can be removed by other biological treatments. The produced biogas can be put on the market or be used for other purposes, improving the energy output of the process. When pretreating lignocellulosic material with $SO_2$ or $H_2SO_4$, the spent liquid may have to be purified from sulphur-containing components, which entails additional costs.

A second advantage of the concept is that the pH in the pretreatment step is higher (usually in the range of 3.3-3.9) than when using inorganic acids which often give rise to a pH-value of 1-2 during pretreatment. Before the pretreated lignocellulosic material is transferred to the hydrolysis and fermentation step(s), the material has to be neutralized. The neutralization is normally performed by means of an addition of a base, such as NaOH, ammonia or lime stone (CaOH). As the pH in the pretreatment step of the present disclosure is not as low as for traditional chemical pretreatment with inorganic acid, lower amounts of base is needed to neutralize the lignocellulosic material before the subsequent step(s).

Another advantage by using a pretreatment method with a pH-value higher than 1-2 is that it is possible to use containers which are less corrosion-resistant than the ones used in traditional chemical pretreatment. This means lower investment costs.

A third advantage may be that by adding organic acid instead of inorganic acid and pretreating the lignocellulosic material at a higher pH-value may affect the formation of degradation products, such as HMF and furfural, which act as inhibitory substances in the subsequent fermentation process. This is because acid treatment with organic acid instead of inorganic acid is milder.

A secondary advantage is that the storing in the presence of organic acids in an atmosphere of low oxygen content is a preservative treatment, which may be particularly beneficial when the supply of raw material is not evenly distributed around the year.

In embodiments of the present disclosure, no organic acid is added in connection with step c). Consequently, in such an embodiment, no acid at all is added during the heating step c). The organic acid present is only added or produced during step a) or b).

In embodiments of the present disclosure, the non-wood lignocellulosic material containing less than 5% (w/w) starch or sugar is selected from lignocellulosic residues of sugar- or starch-containing crops, such as sugar cane or sweet *Sorghum* species.

The lignocellulosic residues of sugar-containing crops may contain remaining sugar, which may be consumed by organic-acid producing bacteria. However, such remaining sugar is only present in low concentrations, such as less than 1% (w/w). Consequently, adding organic-acid producing bacteria in step a) is particularly beneficial when the lignocellulosic material is derived from sugar- or starch-containing crops, since the bacteria may consume the remaining sugar or starch.

In embodiments of the present disclosure, the lignocellulosic material comprises or consists of bagass. Bagass refers to the fibrous residue remaining after sugarcane or sweet sorghum stalks are crushed to extract their juice. The bagass may contain sugar remaining after the extraction of the juice.

Normally, a temperature of at least 180° C. is needed in step c) to obtain an effective pretreatment. However, to avoid excessive energy costs and unwanted or unnecessary degradations, the temperature should not be too high. In embodiments of the present disclosure, the heating of the lignocellulosic material (step c) is performed at a temperature of 180-230° C. In another embodiment of the present disclosure, the heating of the lignocellulosic material is performed at a temperature of 190-230° C., such as 200-220° C. The heating may be performed by adding steam to the organic acid-impregnated lignocellulosic material.

In embodiments of the present disclosure, the heating of the lignocellulosic material (step c) is performed for a period of at least 30 seconds, such as at least 5 minutes, such as 5-20 minutes. In further embodiments of the present disclosure, the heating of the lignocellulosic material (step c) is performed for a period of 5-15 minutes and in yet another embodiment of the present disclosure, the heating of the lignocellulosic material (step c) is performed for a period of 5-10 minutes.

To a certain extent, an increased temperature may compensate for a reduced time, and vice versa.

In embodiments of the present disclosure, the storing in step b) is in an atmosphere containing less than 5% oxygen. In another embodiment of the disclosure, the storing in step b) is in an atmosphere containing less than 2% oxygen. The storing may also be under anaerobic conditions.

As mentioned above, the storing may for example be carried out in a silo, in another form of container or in a stack. During the storing, fresh lignocellulosic material may be added successively. In the case of a stack, the organic acid-impregnated lignocellulosic material may be taken out from the bottom of the stack. The atmosphere in the centre and/or at the bottom of the stack may have the oxygen content of less than 5%. The lignocellulosic material is stored in this environment for at least two weeks before being removed from the stack. In the case of a container, new material may be added on top of the container while the rest of the material may be pushed down. The atmosphere in the middle of the collection of lignocellulosic material has a low content of oxygen, less than 5%. The storing in the atmosphere of reduced oxygen content is at least two weeks long.

In embodiments of the present disclosure, the storing in step b) may be performed for at least 3 weeks. In another embodiment of the present disclosure, the storing in step b) may be performed during at least 4 weeks. As shown in Example 2, a storing period of more than 4 weeks time may not necessary lead to a higher overall yield of sugars.

In embodiments of the present disclosure, the organic acid is selected from formic acid, acetic acid, propionic acid and lactic acid, and the organic acid-producing bacteria are selected from bacteria producing formic acid, acetic acid, propionic acid and lactic acid. The majority of the organic acid or organic acid-producing bacteria are preferably added during step a) of the method. However, additional organic acid or organic acid-producing bacteria may be added during step b). Common lactic acid bacteria are strains of *Lactobacillus*. Examples of lactic acid bacteria are *Lactobacillus plantarum, Lactobacillus buchneri, Enterococcus faecium* and *Pediococcus* species.

In the method of the present disclosure, the organic acid or organic acid-producing bacteria may be added in such an amount that the pH of liquids squeezed out of the organic acid-impregnated material during or after step b) is in the range of 3.1-4.5, such as 3.3-3.9. Consequently, in embodiments of the present disclosure, the pH of liquids from the lignocellulosic material during step b) may be 3.1-4.5, such as 3.3-3.9. For example, such a pH may be maintained during at least 2 weeks, such as at least 3 weeks or 4 weeks.

The material in step b) is normally solid (a high dry contents concentration is beneficial), and to measure the pH in step b), some of the material may thus be pressed or squeezed to extract a liquid of which the pH may be measured.

Alternatively, or as a complement, the pH may be measured after the heat treatment c). The organic acid or organic acid-producing bacteria may be added in such an amount that the pH of liquids squeezed out of the pretreated lignocellulosic material after the completion of step c) is in the range of 2.5-3.7, such as 2.9-3.5. Consequently, in embodiments of the present disclosure, the pH of liquids from the pretreated lignocellulosic material may be 2.5-3.7, such as 2.9-3.5.

In the examples below, the pH of the bagass treated according to the present disclosure was 3.5 during the storing (corresponding to step b)) and 3.1-3.3 after the heating, and such conditions resulted in satisfactory pretreatments (see table 1).

It is a general object to keep the dry solids concentration as high as possible during the pretreatment to avoid dilution of the material, which entails downstream processing costs. However, the dry solids concentration of the lignocellulosic material normally constitutes an upper limit. In embodiments of the present disclosure, the dry solids concentration is 20-50%, such as 30-40%, during step c).

In embodiments of the present disclosure, the method further comprises the steps of d) hydrolyzing, fermenting and distilling the pre-treated lignocellulosic material to obtain an ethanol-containing product and a spent liquid comprising organic components, and e) digesting the spent liquid to produce biogas from the organic components. As mentioned above, the organic acid produced or added in the method may, in contrast to inorganic acids, be converted to biogas in step e).

Biogas may also be produced from a liquid fraction separated from the pretreated lignocellulosic material after the completion of step c). Such liquid fraction comprises organic components, such as pentoses and/or hemicellulose and organic acids, which may be converted to biogas. In embodiments of the present disclosure, the method may thus further comprise the steps of separating a liquid fraction comprising dissolved and/or solubilized organic components from the pretreated lignocellulosic material and digesting at least part of the separated organic components to produce biogas. Such embodiments may be combined with a fermentation that is not adapted for conversion of pentoses to ethanol.

In embodiments of the present disclosure, both types of biogas production described above may be performed in the same method.

The digestions described above are preferably performed under anaerobic conditions. Further, the digestions may be performed using a microorganism selected from bacteria or archaea.

Before the hydrolysis step the pretreated lignocellulosic material may be neutralized. For example the pretreated lignocellulosic material may be neutralized by means of an addition of NaOH or ammonia. Also, lime stone ($Ca(OH)_2$) or magnesium oxide (MgO) may be used.

The hydrolysis and fermentation arrangement may comprise two separate vessels or containers for hydrolysis and fermentation, respectively. Alternatively, it may comprise a single vessel for simultaneous hydrolysis and fermentation. The simultaneous hydrolysis and fermentation (or simultaneous saccharification and fermentation) is sometimes referred to "SSF". In SSF, fermentable sugars are produced by hydrolytic enzymes and continuously fermented by a fermenting agent.

A number of fermenting agents can be used in the fermentation step, for example different types of yeast. A preferred yeast type is the naturally occurring *Saccharomyces cerevisiae* or a modified variant thereof.

The result from the fermentation, the mash, is further transported to a distilling unit. Distillation is the preferred method for separating ethanol from the fermented hydrolyzate due to the lower boiling point of ethanol compared to the other substances in the fermented hydrolyzate.

In the distillation unit, the mash is heated to a boiling point of ethanol which results in that the ethanol is leaving the unit in the form of vapor. The ethanol gas is cooled down and the ethanol-containing product is obtained in the liquid state. The remaining fluid and the solid residues (normally mainly lignin and/or degradation products of lignin) are drained off from the unit.

The hydrolysis of step d) may be enzymatic or acidic. A separate hydrolysis vessel may be adapted for enzymatic or acidic hydrolysis.

When the hydrolysis is enzymatic, SSF may be performed. One of the advantages with SSF is that the yeast ferments the sugar to ethanol as soon as the sugar is set free, and since monomer sugar has a negative effect on the enzymes activity if the sugar concentration is too high, the enzymes will in this way work considerably much more effective.

However, enzymatic hydrolysis may also be performed separate from the fermentation. That is, enzymatic hydrolysis is performed in one step which is followed by the fermentation.

The hydrolysis after the pretreatment of the present disclosure is preferably enzymatic, since in such case, no inorganic acids at all have to be added in the whole ethanol production process.

BRIEF DESCRIPTION OF THE FIGURES

FIG. 1 shows a schematic overview of a process for the production of ethanol. A) shows a process for production of ethanol involving a traditional chemical pretreatment step involving inorganic acid. B) shows a process for production of ethanol with a pretreatment involving addition of organic acid and storing as well as a heating step, according to the method of the present disclosure. C) shows a process for production of ethanol involving a pretreatment step according to the method of present disclosure and an additional step of digesting the spent liquid to biogas.

DETAILED DESCRIPTION OF EXAMPLE EMBODIMENTS

Non-limiting embodiments of the method of the present disclosure are described in more detail below.

Example 1

Method for the Process of Production of Ethanol Comprising a Pretreatment Step including Adding Organic Acid and Storing Organic Acid-impregnated Lignocellulosic Material FIG. 1 illustrates a schematic overview of the process for production of ethanol.

A) shows traditional process for production of ethanol involving a traditional chemical pretreatment step. In the pretreatment step, SO$_2$ is added 1.

B) shows a process for production of ethanol with a pretreatment involving addition of organic acid and storing as well as a heating step, according to the method of the present disclosure. The traditional pretreatment step, shown in FIG. 1A, is thus replaced by a pretreatment involving two phases, see FIG. 1B. First, organic acid or organic acid-producing bacteria are added to non-starch lignocellulosic material from non-wood crops. The lignocellulosic material is stored in an atmosphere having an oxygen content of less than 5% in the presence of organic acid for a period of at least two weeks 2. The organic acid-impregnated lignocellulosic material is then heated to at least 190° C. for at least 5 minutes in a pressurized vessel 3.

After pretreatment, the pretreated lignocellulosic material is transported to a vessel for simultaneous enzymatic hydrolysis and fermentation 4. After fermentation, the mash is distilled in a distillation unit 5. The product is an ethanol-containing product.

C) shows a process for production of ethanol involving a pretreatment according to the method of present disclosure and an additional step of fermenting the spent liquid to biogas. The same procedure is carried out as in FIG. 1B. In FIG. 1C, the spent liquid from the distillation unit is however used for biogas production. The spent liquid, containing for example organic acids and other organic material, is anaerobically digested 6 to biogas under anaerobic conditions using bacteria.

Example 2

Materials and Methods

Samples of bagass and spruce wood chips were pretreated using different conditions.

To a first sample of 0.436 kg bagass (0.140 kg of dry substance), lactic acid was added. The sample was then wrapped in plastics and stored in a substantially anaerobic atmosphere for one month. The storing was followed by heat treatment at 210° C. for five minutes, without the addition of SO$_2$. The heating was performed in a 4-liter stainless steel batch reactor. The heating was performed using injection of direct steam. The heat up period to desired temperature was less than 10 seconds. After the desired reaction time the material was released to a flash vessel at atmospheric pressure. The lactic acid was added in such an amount that the pH of liquid squeezed out of the material before the heating was 3.5. After the steam-treatment, the pH of liquid squeezed out of the pretreated material was about 3.2. The dry solids concentration (DS %) during the heating is shown in table 1.

To a second sample of the same amount of bagass, the same amount of lactic acid was added and the sample was then stored in the same way as the first bagass sample. The storing was followed by heat treatment at 200° C. for five minutes, and in this heat treatment, 2.5% (w/w) SO$_2$ was added. In this case, the pH of liquid squeezed out of the pretreated material was about 1.8 after the steam-treatment.

To a first sample of 1.000 kg spruce wood chips (0.370 kg of dry substance), lactic acid was added. The sample was then wrapped in plastics and stored in a substantially anaerobic atmosphere for one month. The storing was followed by heat treatment at 220° C. for five minutes, without the addition of SO$_2$. Again, the heating was performed in a 4-liter stainless steel batch reactor using injection of direct steam. The heat up period to desired temperature was less than 10 seconds. The lactic acid was added in such an amount that the pH of liquid squeezed out of the material before the heating was 3.1. After the steam-treatment, the pH of liquid squeezed out of the pretreated material was about 3.2.

To a second sample of the same amount of spruce wood chips, the same amount of lactic acid was added, and the sample was then stored in the same way as the first spruce wood sample. The storing was followed by heat treatment at 210° C. for five minutes, and in this heat treatment, 2.5% (w/w) SO$_2$ was added. In this case, the pH of liquid squeezed out of the pretreated material was about 1.5 after the steam-treatment.

Further, a third and fourth sample of 0.436 kg bagass were pretreated in the same manner as the first and second bagass sample, with the exception of that the storing time was two months instead of one. Here, the pH of liquid squeezed out of the material was 3.5 before the steam-treatment and about 3.2 after the steam-treatment.

Also, a third and fourth sample of 1.000 kg spruce wood chips were pretreated in the same manner as the first and second spruce wood sample, also with the exception of that the storing time was two months instead of one.

Finally, as controls, a fifth sample of 0.436 kg bagass was heat treated at 200° C. for five minutes in the presence of 2.5% (w/w) SO$_2$ and a fifth sample of 1.000 kg spruce wood chips was heat treated at 210° C. for five minutes in the presence of 2.5% (w/w) SO$_2$. The pretreatments of these two control samples represent previously described pretreatments.

All the pretreatments were followed by enzymatic hydrolysis (2% (w/w) solid material). After the hydrolysis, the amounts of the monomers glucose, xylose and mannose (only spruce wood) were measured.

Results

The results of the various pretreatments were determined by calculating the overall yields of glucose, xylose and mannose (only spruce wood) as the percentage of the theoretical amount in the raw material. The results are summarized in table 1 below.

|  | 1st bagass | 2nd bagass | 1st spruce | 2nd spruce | 3rd bagass | 4th bagass | 3rd spruce | 4th spruce | 5th bagass | 5th spruce |
|---|---|---|---|---|---|---|---|---|---|---|
| Storing with lactic acid (months) | One | One | One | One | Two | Two | Two | Two | — | — |

-continued

|  | 1st bagass | 2nd bagass | 1st spruce | 2nd spruce | 3rd bagass | 4th bagass | 3rd spruce | 4th spruce | 5th bagass | 5th spruce |
|---|---|---|---|---|---|---|---|---|---|---|
| Heating temp (° C.) | 210 | 200 | 220 | 210 | 210 | 200 | 220 | 210 | 200 | 210 |
| Heating time (min) | 5 | 5 | 5 | 5 | 5 | 5 | 5 | 5 | 5 | 5 |
| Heating DS (%) | 32 | 32 | 37 | 37 | 32 | 32 | 37 | 37 | 33 | 39 |
| $SO_2$-content (%) | 0.0 | 2.5 | 0.0 | 2.5 | 0.0 | 2.5 | 0.0 | 2.5 | 2.5 | 2.5 |
| Overall yield (%) |  |  |  |  |  |  |  |  |  |  |
| Glucose | 85.4 | 84.7 | 31.1 | 75.4 | 80.1 | 76.1 | 24.9 | 67.6 | 82.6 | 73.1 |
| Xylose | 52.3 | 40.6 | 39.1 | 48.6 | 57.4 | 38.9 | 38.0 | 57.4 | 43.7 | 53.9 |
| Mannose | — | — | 67.0 | 65.5 | — | — | 62.3 | 73.2 | — | 65.6 |

The pretreatment of the first bagass sample resulted in a similar glucose yield and a better xylose yield as compared to the pretreatment of the second sample. This shows that the $SO_2$ is superfluous when the bagass has been stored in the presence of the lactic acid. If anything, the $SO_2$ addition appears to have a negative impact on the xylose yield. These conclusions are further supported by comparing the results of the pretreatment of the first bagass sample with those of the pretreatment of the fifth bagass sample; the yields are just as good, if not even better, when the $SO_2$ addition in connection with the heat treatment was replaced by storing in the presence of lactic acid.

However, regarding spruce, the glucose yield in particular, was significantly lower for the treatment without the $SO_2$ addition (first and third spruce sample) than for the treatment with $SO_2$ addition (second and fourth sample), indicating that when spruce wood chips are used as the starting material, the storing in the presence of the organic acid is not sufficient for replacing the $SO_2$ addition. These conclusions are further supported by a comparison of the results of the first or third spruce sample with those of the fifth spruce sample, since the yields were significantly lower when the $SO_2$ addition in connection with the heat treatment was replaced by storing in the presence of lactic acid.

The results of the pretreatment of the third bagass sample is not better than those of the pretreatment of the first bagass sample, indicating that one month is a sufficient storage time.

The invention claimed is:

1. A method for pretreating non-wood lignocellulosic material containing less than 5% (w/w) starch and less than 5% (w/w) sugar for use in a process for production of ethanol from lignocellulose, said pretreating comprising the steps of:
   a) adding organic acid or organic acid-producing bacteria to the lignocellulosic material;
   b) storing the lignocellulosic material in the presence of the organic acid for a period of at least two weeks in an atmosphere of less than 5% oxygen to obtain organic acid-impregnated material; and
   c) heating the organic acid-impregnated material at a temperature of at least 160° C. to obtain pretreated lignocellulosic material,
   wherein no, or substantially no, inorganic acid or base, including $SO_2$, is added in the method.

2. The method according to claim 1, wherein no organic acid is added in connection with step c).

3. The method according to claim 1, wherein said non-wood lignocellulosic material containing less than 5% (w/w) starch and less than 5% (w/w) sugar is selected from bagass, sugar cane trash, wheat straw, rice straw, sorghum species, arundo, mischanthus or agricultural residues.

4. The method according to claim 1, wherein said non-wood lignocellulosic material containing less than 5% (w/w) starch and less than 5% (w/w) sugar is selected from sugar cane bagass or sweet sorghum bagass.

5. The method according to claim 1, wherein said temperature of step c) is at least 180° C.

6. The method according to claim 1, wherein the heating of step c) is performed for a period of at least 30 seconds.

7. The method according to claim 1, wherein the organic acid-impregnated material, if squeezed, produces a liquid having a pH between 3.1 and 4.5.

8. The method according to claim 7, wherein the organic Acid-impregnated material, if squeezed, produces a liquid having a pH between 3.3 and 3.9.

9. The method according to claim 1, wherein said atmosphere of step b) contains less than 3 % oxygen.

10. The method according to claim 1, wherein said period of step b) is at least 3.

11. The method according to claim 1, wherein said organic acid is selected from formic acid, acetic acid, propionic acid or lactic acid and said organic acid-producing bacteria are selected from bacteria producing formic acid, acetic acid, propionic acid or lactic acid.

12. The method according to claim 1, wherein the organic acid-impregnated material has a dry solids concentration of 20-50% during step c).

13. The method according to claim 1, further comprising the steps of;
   d) hydrolyzing, fermenting and distilling the pre-treated lignocellulosic material to obtain an ethanol-containing product and a spent liquid comprising solid and dissolved organic components;
   e) digesting said spent liquid to produce biogas from organic components of said spent liquid, including at least part of said added or produced organic acid.

14. The method according to claim 1, further comprising the steps of separating a liquid fraction comprising dissolved and/or solubilized organic components from the pretreated lignocellulosic material and digesting said liquid fraction to produce biogas from the organic components, including at least part of said added or produced organic acid.

15. The method according to claim 13, wherein said hydrolysis of step d) is enzymatic hydrolysis.

16. The method according to claim 5, wherein said temperature of step c) is at least 190° C.

17. The method according to claim 5, wherein said temperature of step c) is 190-230° C.

18. The method according to claim 6, wherein the heating of step c) is performed for a period of at least 5 minutes.

19. The method according to claim 6, wherein the heating of step c) is performed for a period of 5-20 minutes.

20. The method according to claim 10, wherein said period of step b) is at least 4 weeks.

* * * * *

UNITED STATES PATENT AND TRADEMARK OFFICE
CERTIFICATE OF CORRECTION

PATENT NO. : 8,835,156 B2
APPLICATION NO. : 13/381380
DATED : September 16, 2014
INVENTOR(S) : Bjornsson et al.

Page 1 of 1

It is certified that error appears in the above-identified patent and that said Letters Patent is hereby corrected as shown below:

On Title Page and In the Specification:
Item (54) and Column 1, Line 2, Title: Please correct "LIGNOCELLUIOSIC"
to read -- LIGNOCELLULOSIC --

In the Claims:
Column 12, Claim 8, Line 39: Please correct "Acid-impregnated material,"
to read -- acid-impregnated material, --

Column 12, Claim 10, Line 44: Please correct "at least 3."
to read -- at least 3 weeks. --

Signed and Sealed this
Third Day of February, 2015

Michelle K. Lee
*Deputy Director of the United States Patent and Trademark Office*